(12) United States Patent
Bert et al.

(10) Patent No.: US 9,330,886 B2
(45) Date of Patent: May 3, 2016

(54) IRRADIATION INSTALLATION AND CONTROL METHOD FOR CONTROLLING SAME

(75) Inventors: Christoph Bert, Uttenreuth (DE); Eike Rietzel, Weiterstadt (DE)

(73) Assignee: GSI Helmholtzzentrum fur Schwerionenforschung GmbH, Darmstadt (DE)

(*) Notice: Subject to any disclaimer, the term of this patent is extended or adjusted under 35 U.S.C. 154(b) by 0 days.

(21) Appl. No.: 14/112,780

(22) PCT Filed: Apr. 20, 2012

(86) PCT No.: PCT/EP2012/001705
§ 371 (c)(1),
(2), (4) Date: Jan. 10, 2014

(87) PCT Pub. No.: WO2012/143134
PCT Pub. Date: Oct. 26, 2012

(65) Prior Publication Data
US 2014/0166896 A1    Jun. 19, 2014

(30) Foreign Application Priority Data
Apr. 21, 2011    (DE) .................... 10 2011 018 613

(51) Int. Cl.
*H01J 37/304* (2006.01)
*H01J 37/317* (2006.01)
*A61N 5/10* (2006.01)

(52) U.S. Cl.
CPC ............. *H01J 37/304* (2013.01); *A61N 5/1067* (2013.01); *H01J 37/317* (2013.01); *A61N 5/1044* (2013.01); *A61N 2005/1087* (2013.01)

(58) Field of Classification Search
CPC ............. A61N 5/1044; A61N 5/1067; A61N 2005/1087; H01J 37/304; H01J 37/317
USPC ............................... 250/397, 492.3
See application file for complete search history.

(56) References Cited

U.S. PATENT DOCUMENTS

| 6,437,513 B1 * | 8/2002 | Stelzer | H01J 47/02 250/283 |
| 6,614,038 B1 * | 9/2003 | Brand | A61N 5/1043 250/396 R |

(Continued)

FOREIGN PATENT DOCUMENTS

| JP | S63953 | 1/1988 |
| JP | 2002191709 | 7/2002 |

(Continued)

OTHER PUBLICATIONS

English Translation of the International Preliminary Examination Report International App. No. PCT/EP2012/001705 International Filing Date: Apr. 20, 2012 Dated: Oct. 22, 2013.

(Continued)

*Primary Examiner* — Wyatt Stoffa
(74) *Attorney, Agent, or Firm* — Reising Ethington PC

(57) ABSTRACT

To control of an irradiation installation, a particle beam is generated with a beam intensity, and a beam quality of the particle beam is monitored with a beam monitoring device. One of several adjustable measurement ranges is selected, wherein the measurement range of the beam monitoring device is set depending on the beam intensity of the particle beam and/or depending on a particle count to be applied.

12 Claims, 7 Drawing Sheets

(56) References Cited

U.S. PATENT DOCUMENTS

| | | | | |
|---|---|---|---|---|
| 6,774,383 B2* | 8/2004 | Norimine | A61N 5/1048 | 250/492.3 |
| 6,799,068 B1* | 9/2004 | Hartmann | A61N 5/1048 | 607/2 |
| 6,885,007 B2* | 4/2005 | Donaghue | G01T 1/244 | 250/200 |
| 7,515,681 B2* | 4/2009 | Ebstein | G01T 1/02 | 378/19 |
| 2003/0076926 A1* | 4/2003 | Renner | A61N 5/1048 | 378/65 |
| 2003/0204336 A1* | 10/2003 | Ritt | A61N 5/1048 | 702/49 |
| 2004/0114716 A1* | 6/2004 | Cole | G01N 23/223 | 378/57 |
| 2005/0238134 A1* | 10/2005 | Brusasco | A61N 5/10 | 378/6 |
| 2006/0033042 A1* | 2/2006 | Groezinger | A61N 5/1043 | 250/492.1 |
| 2007/0045546 A1* | 3/2007 | Hsi | G01T 1/02 | 250/361 R |
| 2007/0051905 A1* | 3/2007 | Fujimaki | H05H 7/10 | 250/492.3 |
| 2007/0181815 A1* | 8/2007 | Ebstein | G01T 1/02 | 250/370.11 |
| 2007/0252093 A1* | 11/2007 | Fujimaki | A61N 5/1048 | 250/492.3 |
| 2007/0257210 A1* | 11/2007 | Wang | H01J 37/304 | 250/492.21 |
| 2008/0027898 A1 | 1/2008 | Matsuo et al. | | |
| 2008/0067405 A1* | 3/2008 | Nihongi | A61N 5/1048 | 250/398 |
| 2008/0073584 A1* | 3/2008 | Callahan | H01J 37/3171 | 250/492.21 |
| 2008/0078942 A1* | 4/2008 | Rietzel | A61N 5/1043 | 250/396 R |
| 2008/0173811 A1* | 7/2008 | Kobayashi | H01J 37/244 | 250/292 |
| 2009/0200476 A1* | 8/2009 | Brusasco | A61N 5/1048 | 250/370.07 |
| 2009/0206273 A1* | 8/2009 | Olson | H01J 37/304 | 250/397 |
| 2009/0299634 A1* | 12/2009 | Schaffner | A61N 5/1048 | 702/1 |
| 2009/0321656 A1* | 12/2009 | Rietzel | G01T 1/2935 | 250/397 |
| 2010/0171504 A1* | 7/2010 | Nichiporov | A61N 5/1048 | 324/464 |
| 2010/0329423 A1* | 12/2010 | Oreper | A61B 6/032 | 378/65 |
| 2011/0027853 A1* | 2/2011 | Bert | A61N 5/1048 | 435/173.1 |
| 2011/0049372 A1* | 3/2011 | Iseki | A61N 5/1043 | 250/362 |
| 2011/0065974 A1* | 3/2011 | Rietzel | A61N 5/103 | 600/1 |
| 2011/0073777 A1* | 3/2011 | Pandolfi | H01J 37/304 | 250/492.3 |
| 2011/0101236 A1* | 5/2011 | Cameron | A61N 5/10 | 250/396 ML |
| 2011/0186746 A1* | 8/2011 | Drees | A61N 5/10 | 250/397 |
| 2011/0231147 A1* | 9/2011 | Takayanagi | G01T 1/29 | 702/150 |
| 2011/0303857 A1* | 12/2011 | Bert | A61N 5/10 | 250/492.1 |
| 2012/0029862 A1* | 2/2012 | Scholz | A61N 5/1031 | 702/127 |
| 2012/0187314 A1* | 7/2012 | Bert | A61N 5/103 | 250/492.3 |
| 2012/0228493 A1* | 9/2012 | Gottschalk | A61N 5/1043 | 250/307 |
| 2012/0238795 A1* | 9/2012 | Bert | A61N 5/1043 | 600/1 |
| 2012/0326029 A1* | 12/2012 | Morton | G01N 23/06 | 250/310 |
| 2015/0071408 A1* | 3/2015 | Ebstein | A61N 5/1075 | 378/65 |

FOREIGN PATENT DOCUMENTS

| | | | | |
|---|---|---|---|---|
| WO | WO 2010034419 A1 * | 4/2010 | | A61N 5/10 |
| WO | 2011006733 | 1/2011 | | |
| WO | WO 2011006733 A1 * | 1/2011 | | A61N 5/103 |
| WO | WO 2011/026697 | 3/2011 | | |

OTHER PUBLICATIONS

Takuji Furukawa, et al. "Design study of a raster scanning system for moving target irradiation in heavy-ion radiotherapy" 1085 Med. Phys. Research Group 34 (3) Mar. 2007.

Shinichi Minohara, et al "Recent Innovations in Carbon-Ion Radiotherapy" J. Radiat. Res., 51, 385-392 (2010), Nat. Inst. of Radiological Sciences, Japan.

PCT Search Report and Written Opinion, Int. Nat. Serial No. PCT/EP2012/001705 Filing Date: Apr. 20, 2012 Priority Date: Apr. 21, 2011, 9pgs.

Japanese Office Action, Application No. 2014-505541, Date of Drafting: Aug. 5, 2015, Representative/Applicant: Okabe, Yuzuru, et al.

* cited by examiner

IRRADIATION INSTALLATION AND CONTROL METHOD FOR CONTROLLING SAME

GENERAL DESCRIPTION

The present disclosure relates to an irradiation system with a particle accelerator with which a particle beam can be generated, wherein the beam qualities of the particle beam can be monitored with a beam monitoring device. Further, the present disclosure relates to a control method for controlling such an irradiation system. Embodiments of the present disclosure are employed in particular within the scope of particle therapy, in which case e.g. patients are irradiated.

Particle therapy is an established method for treatment of tissue, in particular tumor diseases. Irradiation methods, as employed in particle therapy, however are also used in non-therapeutic fields. For example, this includes research within the scope of particle therapy, e.g. for product development, which is carried out on non-living phantoms or bodies, irradiation of materials etc.

Herein charged particles such as protons or carbon ions or other ions are accelerated to high energies, formed into a particle beam and guided via a high energy beam transport system to one or more irradiation chambers. In the irradiation chamber the target volume to be irradiated is irradiated with the particle beam.

In order to guarantee the success of the irradiation and the safety of the irradiation beam qualities of the particle beam are continuously monitored.

For example, this is done using a beam monitoring system in which both intensity measurement chambers and also position measurement chambers are used. Both measurements are usually performed redundantly so that even in the case of error of one of the two systems a second system is available. The security in the beam application is increased as a result.

The intensity measurement chamber can for example be used in the controlling of irradiation in the raster scan method. In the raster scan method a plurality of target points in the target volume are successively approached by a particle beam and at each target point a pre-determined particle count is deposited. With the intensity measurement chamber the particle count deposited by the beam is monitored as beam quality, so that the particle beam can be moved to the next target point as soon as the required particle count has been deposited on the current target point.

Limitations within the measurement of the beam intensity occur when having low intensity due to the signal to noise ratio of the measurement chambers and when having high intensity by a possible saturation of the measurement chambers. Due to the great ranges in which the beam quality of the particle beam shall be measured, the measurement chambers or the amplifiers or other devices in the measurement chain which detect the charge generated in the chamber, usually exhibit several measurement ranges.

An irradiation of a target volume can take place in iso-energy layers. The target volume is sectioned into iso-energy layers, wherein each iso-energy layer correlates to an energy of the particle beam. The irradiation of the iso-energy layers takes place successively by adaptation of the energy of the particle beam to the respective iso-energy layer to be irradiated.

The present disclosure addresses the problem of providing an irradiation system which allows for secure irradiation of the target volume and at the same time favorable and fast control of the irradiation system. The present disclosure further addresses the problem of specifying a corresponding control method for carrying out irradiation.

This problem is solved by the independent claims. Preferred embodiments of the present disclosure are specified in the dependent claims and will be described in greater detail in the following. The preceding and following description of the individual features relates both to the device category and also the method category without this being explicitly mentioned specifically in each case; the individual features disclosed in the process can be useful to the present disclosure in other combinations than those shown.

The irradiation installation comprises an accelerator system with a particle accelerator, with which particles can be accelerated and with which a particle beam can be generated, wherein the particle beam exhibits a beam intensity, at least one beam monitoring device for the measurement of a beam quality of the particle beam, wherein the beam monitoring device exhibits several adjustable measurement ranges; and a control device for controlling the acceleration device and the beam monitoring device, wherein the measurement range of the beam monitoring device can be set dependent on the beam intensity of the particle beam and/or on a particle number to be applied and which for example can be altered during an irradiation.

The beam quality measured by the beam monitoring device is for example the beam intensity and/or the transverse beam position.

In previous irradiation systems or irradiation methods it was necessary to make sure that the dose to be applied could be exactly monitored. This was achieved by setting the intensity of the particle beam and the measurement ranges of the beam monitoring devices based on the special requirements that are predefined by a therapy plan. The irradiation of the target volume took place with these settings.

However, it was recognized that this rigid specification led to a disadvantageous control of the irradiation system. For example, an irradiation plan can require that a beam with low intensity is to be used and that the measurement ranges of the beam monitoring device must be adjusted accordingly, since for example one target point in the therapy plan with a low particle count is present so that the monitoring of the dose deposition at this target point can only be securely guaranteed with these settings. This however means that it is also necessary to approach the other target points of the therapy plan with these settings, therefore also target points at which a significantly higher particle count is deposited. This may lead to a comparatively long irradiation time.

The method can be designed more flexibly designed if the system is controlled e.g. via the control device to the effect that the selection of the active measurement range of the beam monitoring system is varied or altered during the irradiation. This change can be performed dependent on the respective particle count to be applied and/or dependent on adjustable beam intensity.

If the particle count to be applied in a specified irradiation section is low or if the beam intensity is low, few charges are induced in the beam monitoring device. For a correct measurement of the beam quality a higher amplification of the signals induced in the beam monitoring device is necessary. Inversely, if the particle count to be applied or the beam intensity is high, many charges are induced. For a correct measurement of the beam quality a lower amplification of the signals induced in the beam monitoring device is necessary, thus a different measurement range of the beam monitoring device. Thus e.g. the amplification of the signals induced in the beam monitoring device is changed in dependency of the beam intensity of the particle beam and/or of the particle count to be applied, e.g. by means of a switchable amplifier chain.

Thus it is possible to perform the irradiation faster since the particle beam can be adjusted to the particle count to be applied during the irradiation, e.g. during the beam application to a target volume, and thus also the required measurement ranges for correct beam monitoring can be adjusted. Thus the irradiation time can be significantly reduced by the present disclosure.

In an embodiment, the control device can be designed for carrying out irradiation of a target volume in the scanning method, wherein the measurement range can be set depending on a particle count to be applied per target point in the target volume at least temporarily during the irradiation of the target volume.

In this way, for example the measurement range can be changed when the change allows for a faster irradiation of the target point to be irradiated. The setting of the measurement ranges can be retained until it is necessary to approach a new target point which makes an adjustment of the measurement range necessary. For example, this can occur when the secure dose application of the new target point can no longer be guaranteed with the previously set measurement range. Depending on the switching time, which is usually predefined by the accelerator system, it can be necessary to make adjustments already during irradiation or for the irradiation of target points prior to the critical target point which requires for a switch.

In another embodiment, the control device can be designed to carry out the irradiation of a target volume slice by slice in iso-energy layers. In this case, the control device can be designed such, that the measurement range of the beam monitor device can be changed during irradiation of an iso-energy layer. This allows for adapting irradiation not only from one iso-energy layer to the next iso-energy layer, but even within an iso-energy layer.

The control device may in another embodiment be designed for application of the irradiation in the rescanning method. In the case of such an irradiation method parts of the target volume are irradiated within one irradiation session in several consecutive rescan passes. The measurement range of the beam monitoring device can be altered then during a rescan pass.

The rescanning method is a special method which is employed to irradiate moved target volumes. By means of uncorrected, multiple application of the irradiation plan for the plan target volume (cf. ICRU) a total dose is deposited in an irradiation session by proportionally lower doses per single application, wherein the total dose on average matches the intended dose distribution in the clinical target volume (cf. ICRU), since by the number of multiple irradiations a defective dose deposition can be averaged due to the movement of the target volume.

By the proportionally lower dose per rescan-pass however significantly fewer charge carriers are induced in the beam monitoring device than in the case of conventional irradiation. It was then recognized that in the case of rigid definition of beam intensity/measurement range this can lead to significantly longer irradiation times, especially in the rescanning method. In this respect the irradiation system, which is designed for carrying out a rescanning method, works well, since now by the flexible adjustment of the measurement ranges of the beam monitoring device improved irradiation speed can be achieved. Without the disclosed embodiment, the irradiation times in the rescanning method would be very long. However, it was realized that rescanning only works well when all movement phases of the target volume movement participate uncoordinated to the movement of the particle beam. Therefore a slowed down irradiation could partially cancel the averaging effects in the rescanning method, e.g. as soon as irradiation duration lies in the magnitude of the target volume movement duration.

Now, the beam intensity of the particle beam can be flexibly controlled, for example by controlling the extraction mechanism in the case of a synchrotron or by controlling the beam intensity provided by the source in the case of a cyclotron, and geared the controlling the measurement range can be selected flexibly during the irradiation. Thus for example the beam intensity can be altered during the irradiation, e.g. due to the particle counts per target point stored in an irradiation plan, and the measurement device can be switched from a first measurement range to a second measurement range during the irradiation, as soon as the beam intensity exits the first measurement range and/or enters the second measurement range.

The irradiation device can be designed such that—when it becomes necessary to switch the measurement range—the particle beam is briefly interrupted and the measurement range is switched during the beam pause. In this way it is possible to prevent the beam being applied at a time when no measurement range is available for monitoring of the beam quality. In this way e.g. in the case of intensity measurement chambers the charge integration can be carried out continuously and the dosimetry can therefore be precisely monitored.

However, this is not always necessary. Switching of the measurement range can also take place during a beam application or in the case of an activated particle beam. In this case there may be the risk that e.g. in the case of intensity monitoring not the entire beam could be recorded. If the time span during which the measurement range is switched is however sufficiently short and/or only a beam with low intensity is being applied, the imprecision that occurs in the event of the beam monitoring can also lie within a tolerable range.

In an embodiment, the beam monitoring device comprises at least two measurement devices, with which the same beam quality can be measured. These measurement devices can for example be used for redundant measurement of the beam quality, e.g. beam intensity or transverse beam position. The measurement devices themselves each exhibit different measurement ranges and the measurement devices can be set such that they are operated at least sporadically in different measurement ranges. Therefore, the implementation of a switching of the measurement range of the beam monitoring device can be improved, since different, simultaneously active measurement ranges are already present within the beam monitoring device. A rapid switch can then for example take place by changing from the one measurement device (which is operated in the first measurement range) to the other measurement device (which is being operated in the second measurement range), without an appreciable or problematic gap occurring in the beam monitoring.

In one embodiment one of the measurement devices can be operated as the main measurement device and another one of the measurement devices can be operated as a redundancy measurement device. The main measurement device and the redundancy measurement device can be operated in a different measurement range. For example, the main measurement device can be operated in a measurement range which is best suited for the desired beam quality, while the redundancy measurement device is operated in an adjacent measurement range, that is, in a non-ideal measurement range. However, the lower accuracy that can be achieved thereby can be sufficient for the redundant measurement, since the applied dose can still be checked at least with respect to its order of magnitude, and hence the beam can be switched off in the case of relevant false dosing. However, in case the measurement range has to be changed, a measurement device with a different measurement range is already actively present. As a result shifting is made possible, easily and simply.

In case the measurement range of the beam monitoring device has to be shifted, in the case of several measurement devices it is possible to switch to the measurement ranges of the individual measurement devices in sequence. In this way it is possible to perform continuous measurements, only for the respective short switching time is a redundancy measurement dispensed with.

The control method for controlling an irradiation installation comprises the following steps:
Generation of a particle beam, wherein the particle beam exhibits a beam intensity,
Monitoring of a beam quality of the particle beam with a beam monitoring device, wherein one of several adjustable measurement ranges is selected, wherein the measurement range of the beam monitoring device is set and changed during irradiation, e.g. depending on the beam intensity of the particle beam and/or depending on a particle count to be applied.

DESCRIPTION OF THE DRAWINGS

Embodiments of the present disclosure with improvements in accordance with the features of the dependent claims will be described in greater detail with the help of the following drawings, however without being limited to said description. The figures show the following:

DETAILED DESCRIPTION

Figure 1:
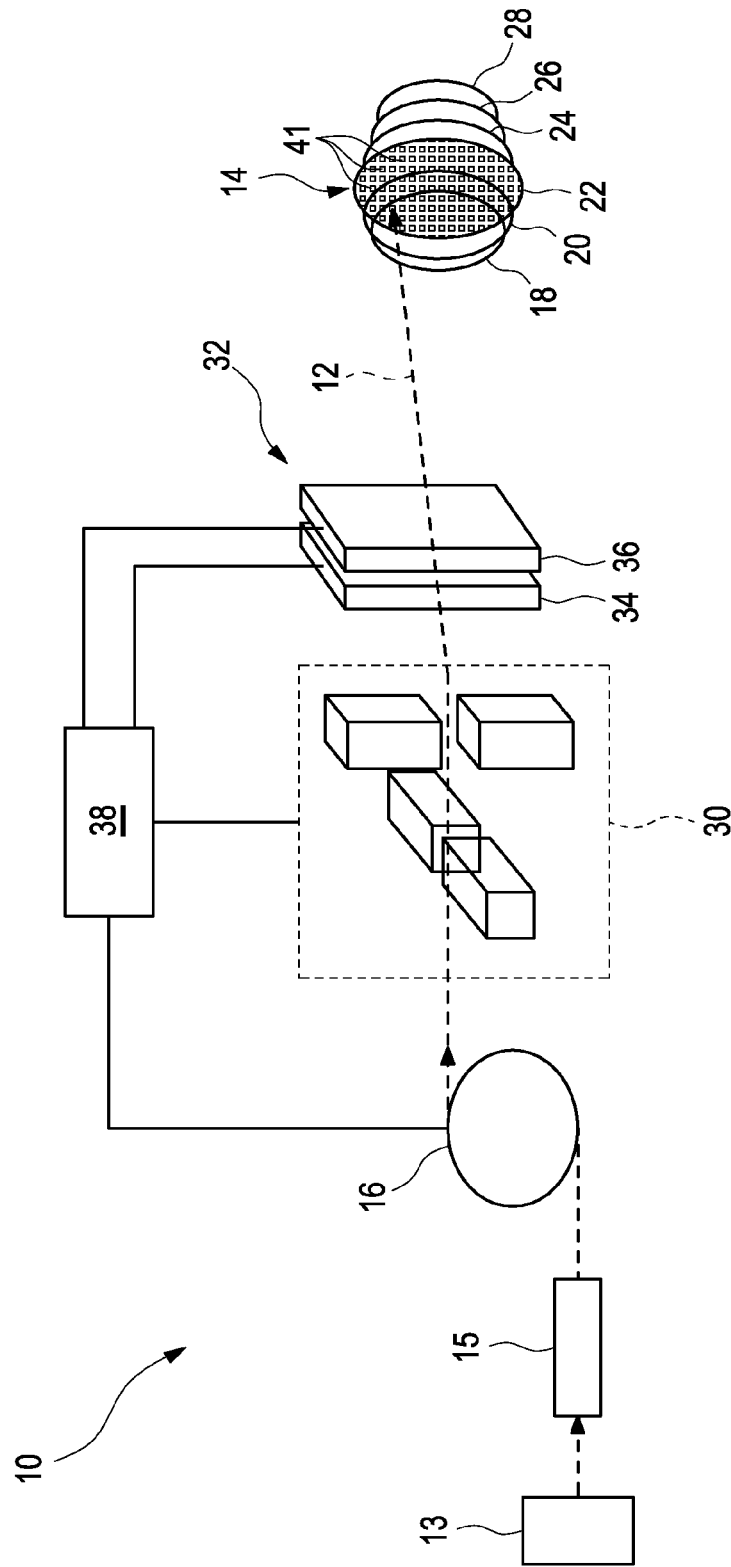
FIG. 1 shows a schematized representation of a particle therapy system in which a target volume is irradiated, wherein the target volume comprises a plurality of target points which are arranged in iso-energy layers.

FIG. 1 shows in schematized representation a set-up of an irradiation system constructed as a particle therapy system 10. The particle therapy system 10 is used for irradiation of a target volume, which is typically positioned with a positioning device, with a beam of particles, said beam of particles being referred to in the following as particle beam 12. For example, a tumor-infected tissue of a patient can be irradiated with the particle beam 12. Provision is likewise made to use the particle beam installation 10 for the irradiation of a non-living body, e.g. of a water phantom or other phantom. The irradiation of the water phantom can for example take place for the purpose of checking and verifying irradiation parameters before and/or after an irradiation of a patient. However, provision is also made to irradiate other bodies, for example experimental assemblies such as cell cultures or bacteria cultures with the particle beam 12. In all cases the target volumes 14 can be moving or resting.

The particle therapy system 10 typically comprises a particle source 13 and an accelerator unit—e.g. a synchrotron 16 and a pre-accelerator 15 or a cyclotron or some other accelerator—which provides a particle beam 12 with the required energy for irradiation. Predominantly particles such as protons, pions, helium ions, carbon ions or the ions of other elements are used. Typically a particle beam 12 has a beam half width of 3-10 mm. The particle beam 12 is transported to an irradiation chamber in which the target volume 14 is located.

In the target volume 13 to be irradiated iso-energy layers 18, 20, 22, 24, 26 and 28 are indicated. An iso-energy layer 18, 20, 22, 24, 26 or 28 corresponds to the penetration depth of the Bragg peak for a specified energy of the particle beam 12.

Preferably a raster scan method is used as a scanning method, wherein in the raster scan method a particle beam 12 is guided from target point to target point without obligatory shutdown in the case of a transition from one target point to the next. The target points are marked with reference numeral 41. A spot scan method with shutdown of the particle beam between the individual target points or other scanning methods such as for example continuous scanning methods can also be used. In FIG. 1 the scanning method is schematically illustrated, with the help of some target points 41 indicated partially in a target volume 14, wherein the target volume 14 is constructed in layers and wherein the target points are successively approached with the particle beam 12.

For execution of the scanning method a scanning device 10 with several deflecting magnets is provided, wherein the deflecting magnets are arranged preferably in two orthogonal directions, allowing the particle beam 12 to be guided from target point 41 to target point 41.

Further a beam monitoring device 32 arranged between the scanning device 30 and the target volume 14 is provided, with which a beam quality of the particle beam 12 can be verified, for example the particle count applied by the particle beam 12 can be verified using an ionization chamber or the position of the particle beam 12 can be verified using a position measurement chamber. In the beam monitoring device a first and a second measurement device 34, 36 are used for measurement of the same beam quality.

A control device 38 controls the installation. The control device 38 for example can control the accelerators 15, 16 for provision of a beam with a desired intensity, direct the beam in accordance with an irradiation plan with the scanning device 30, and evaluate the measurement data of the beam monitoring device 32 for monitoring of the beam quality. In addition the control device 38 can select one of several measurement ranges, in which the beam monitoring device 32 or its measurement devices 34, 36 are used. The control device 38 is typically divided into several subunits connected to one another (not shown here for the sake of clarity).

Figure 2:
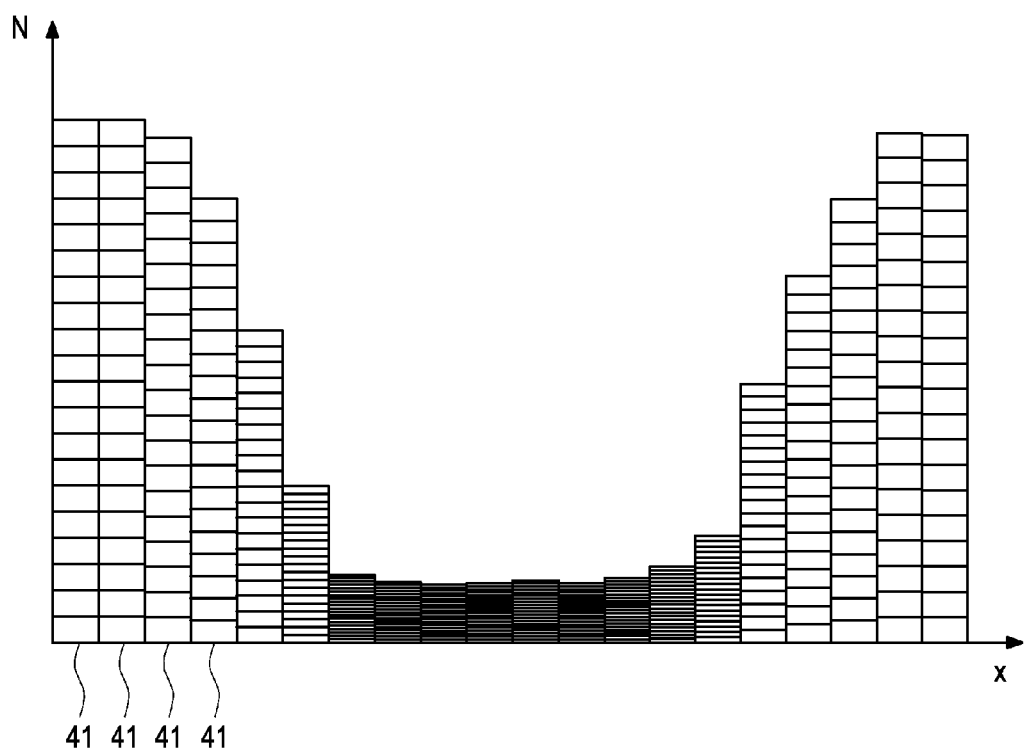
FIG. 2 shows the representation of a varying particle count distribution which is supposed to be applied to target points arranged adjacent to one another within an iso-energy layer.

FIG. 2 shows the particle count which is to be applied with the middle iso-energy layer 22, for some target points of this layer. The x-axis denotes the location x of target points 41 along a line within the middle iso-energy layer, the y-axis denotes the particle count N to be applied.

The total dose to be applied is to be applied in the rescanning method. The middle iso-energy layer may be approached with 20 rescan passes, wherein each target point 41 of the iso-energy layer is approached each time and per approach a single dose is applied which is lower than the total dose to be applied, so that the single doses sum up to the total dose to be applied.

The particle count to be applied fluctuates greatly within the iso-energy layer. This can occur for example if in the case of an elliptical target volume in the central regions of the iso-energy layer a preliminary dose has been deposited by the irradiation of the distal iso-energy layers, but the edge regions of the iso-energy layer have not.

A similar, analogous case can often occur when the target volume is volumetrically scanned, thus when the scanning is not only done within an iso-energy layer, but rather when the scanning is carried out also in the direction of the particle beam. Vast fluctuations of the particle counts to be applied in an irradiation section can also occur in volumetric scanning, since a preliminary dose by irradiation of the distal target points has been deposited at proximal target points already.

In the middle region of the iso-energy layer only a very low single dose is hence applied per approach of target points 41.

If this low single dose determines the particle beams' beam intensity in the irradiation of the overall iso-energy layer, and thus in correlation to the beam intensity also the measurement range with which the beam monitoring device must be operated in order to securely detect the low single dose, this would mean that the irradiation of the iso-energy layer would last for a comparatively long time.

The irradiation of the target points where a high particle count is to be applied can take longer by a factor of 10 as compared to irradiation of target points where a lower particle number is to be applied (e.g. central target points versus peripheral target points, or distal target points versus proximal target points).

With the help of FIG. 3 through FIG. 6 embodiments of the present disclosure are described with which this problem can be avoided.

Figure 3:
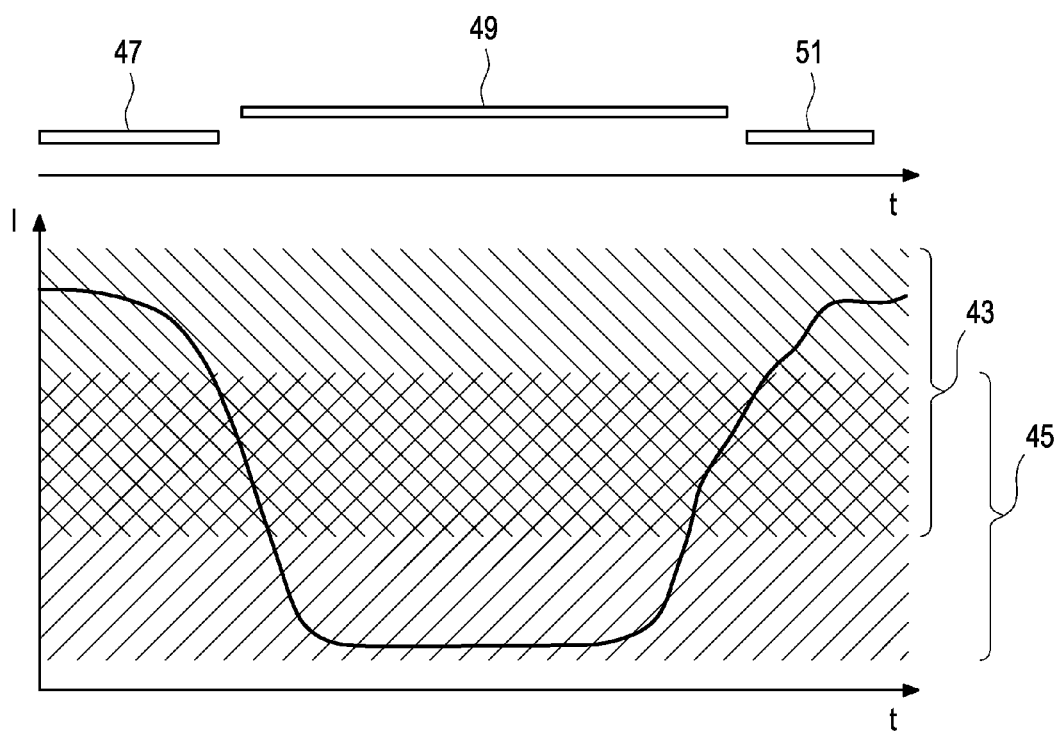
FIG. 3 shows a representation for explanation of the measurement range coordination of a beam monitoring device to the intensity of the particle beam.

FIG. 3 shows in the bottom part the course of the beam intensity I over the time t, as it can be set during a rescan pass for the irradiation of a layer as shown in FIG. 2. The time-dependent course of the beam intensity follows the different particle counts which are supposed to be applied from target point 41 to target point 41.

The beam intensity can be controlled by the control device of the system for example in the case of a synchrotron by having the knock-out mechanism with which the beam is kicked out of the synchrotron, wherein the knockout-mechanism is actuated corresponding to the desired particle count stored in the irradiation plan. By selection of the intensity of the magnetic field or of the frequency of the magnetic field or of the electrostatic field of the knock-out mechanism the intensity of the extracted particle beam can be increased or lowered. In case the system is operated with a cyclotron as an accelerator, the beam intensity can be controlled by controlling the intensity of the particles emitted from the particle source.

In the lower part of FIG. 3 two measurement ranges 43, 45 of a measurement device are drawn in. The measurement device can monitor a beam quality of the particle beam such as e.g. the intensity of the particle beam with an intensity measurement chamber or the position of the particle beam with a position measurement chamber, e.g. with a MWPC (multi wire proportional chamber).

In the case of an intensity controlled scanning method the control of the particle beam is triggered to the next raster point as soon as the required particle count is deposited at the current raster point. With the intensity measurement chamber on the one hand the particle count deposited by the beam is monitored as beam quality, so that the particle beam can be directed to the next target point as soon as the required particle count has been deposited on the current target point, and on the other hand the measurement range of the monitoring device 32, which comprises the intensity measurement chamber, is changed during the irradiation depending on the beam intensity of the particle beam 12 and/or depending on the particle count to be applied. In other words, the measurement range of the beam monitoring device 32 is adjusted during the irradiation to the beam intensity of the particle beam 12 and/or to the particle count to be applied for the next target point.

With the first, upper measurement range 43 the measurement device is operated in such a way that e.g. by suitable amplification of the voltage signals, which are induced by the particle beam and recorded, the particle beam can be sufficiently precisely recorded if its intensity I is in this range. In the second, lower measurement range 45 the measurement device records the particle number sufficiently precisely when its intensity is in the corresponding range.

The first measurement range 43 and the second measurement range 45 can—as shown here—overlap to a certain degree. The measurement device will ordinarily exhibit further measurement ranges, which are not drawn in here for the sake of clarity.

Above the diagram the time activation of the two measurement ranges 43, 45 is shown. First, the measurement device is operated in the first measurement range 43 (shown by the left bar 47), then the measurement device is switched to the second measurement range 45 (represented by the middle 49 bar) and later in the course there is a switch again to the first measurement range 43 (represented by the right bar 51). The selection of the respective measurement range 43, 45 is hence adjusted to the course of the intensity I of the particle beam.

This adaptation of the measurement range can be coordinated with the intensity I of the particle beam, by using the control parameters which set the intensity I also for selection of the measurement ranges 43, 45 or by measuring the intensity I of the particle beam and predefining the measurement range 43, 45 according to the result of the intensity measurement. Alternatively, this selection can be set together with the intensity I of the particle beam, for example by predefining the selection of the measurement range 43, 45 through the predefined particle count N to be applied at a target point.

The shifting procedure from the first measurement range 43 to the second measurement range 45 requires a certain switching time, during which the measurement device does not produce utilizable signals. If the particle beam has low intensity I, or, as the case may be, in the case of a low particle count and in the case of a short switching time this can however be tolerated, since only a little information about the applied dose is lost.

The scan path, which is the sequence with which the individual target points in the target volume are scanned, is associated with the necessary switching procedures of the measurement ranges. By skillful selection of the scan path the number of necessary switches can be reduced, e.g. by preferably approaching those target points in succession that are monitored by the same measurement range. In other words, in the case of this exemplary embodiment the scan path is selected depending on the number of necessary switches of the measurement ranges. This is managed by taking into consideration the number of necessary switches e.g. in the irradiation planning phase, in which the scan path is defined. It is also conceivable to define the scan path online, which is during the irradiation, in consideration of the number of necessary switches. This functionality can be provided by the control device and/or by an irradiation planning device.

Figure 4:
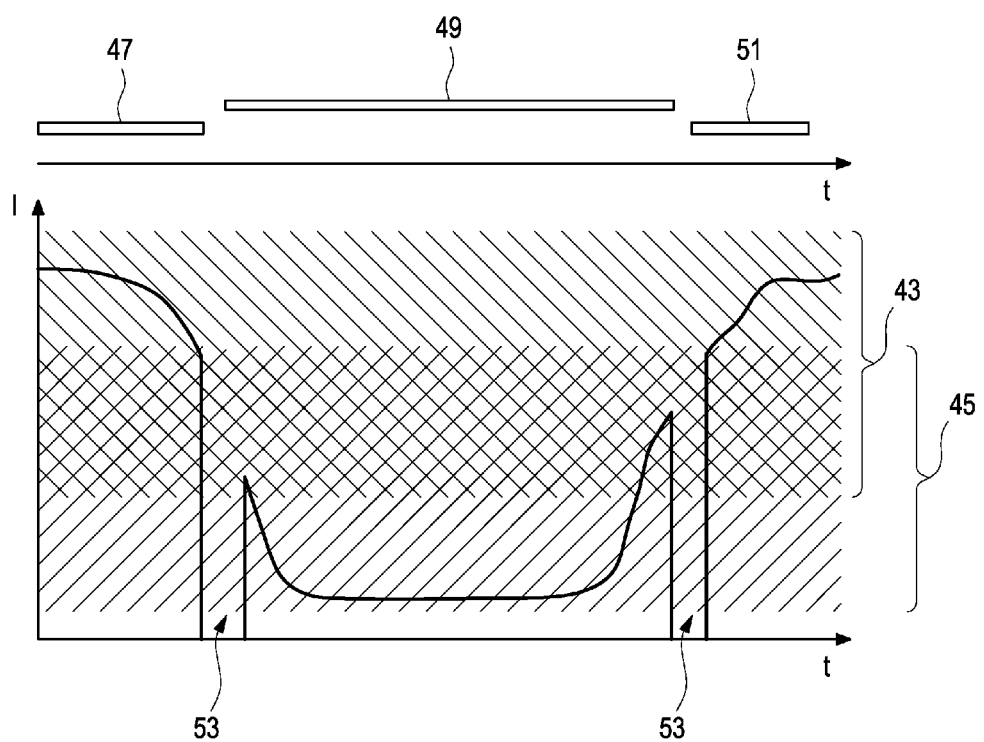
FIG. 4 shows a representation similar to FIG. 3, which shows a brief beam interruption during the switch of the measurement ranges.

FIG. 4 shows an embodiment slightly modified in comparison to FIG. 3. The measurement range 43, 45 is not switched while the particle beam is operating, but rather with the introduction of a brief beam interruption 53. As soon as it is determined that the intensity change of the particle beam requires an adjustment of the measurement range 43, 45 a brief beam interruption 53 is induced. This can take place for example by switching off the knock-out extraction mechanism for a synchrotron or by activating a kicker magnet in the high energy beam transport system, said kicker magnet briefly diverts the beam from the regular beam course. During the brief beam pause the switch of the measurement range 43, 45 takes place. Subsequently the beam interruption 53 is terminated.

Figure 5:
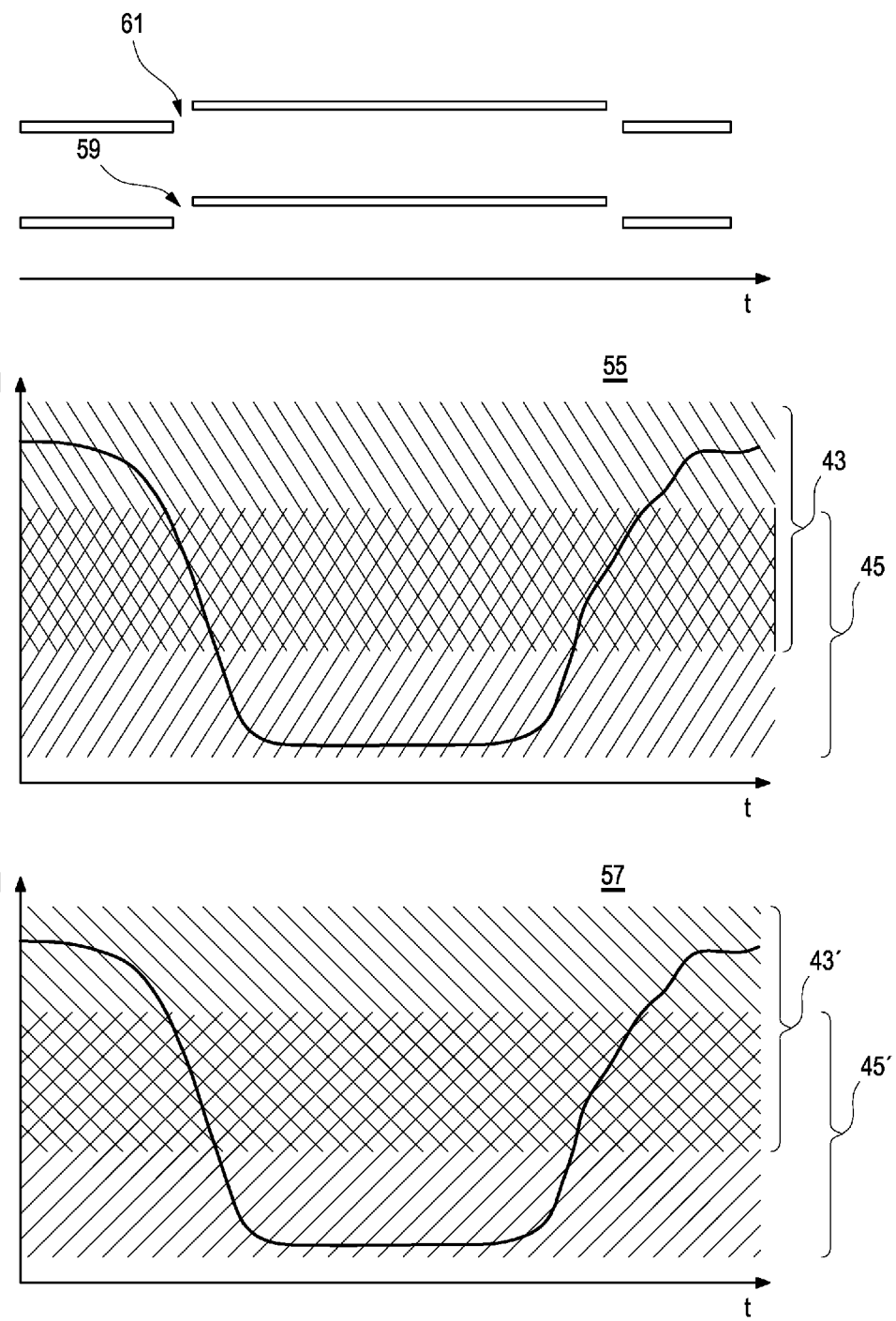
FIG. 5 shows a representation for explanation of an embodiment in which two measurement devices are used in the beam monitoring device for monitoring the beam quality.

FIG. 5 shows an embodiment in which the beam monitoring device exhibits a first measurement device (representation of the measurement ranges of the first measurement device in the middle part 55 of FIG. 5) and a second measurement device (representation of the measurement ranges of the second measurement device in the lower part 57 of FIG. 5) for measurement of the same beam quality.

The two measurement devices are usually operated in such a way that the beam quality to be measured is redundantly measured with both measurement devices. To this end the two measurement devices are usually operated in the same measurement range. However, in case a switch of the measurement range becomes necessary, the two measurement devices can be operated in the embodiment shown here such that at least one of the two measurement devices provides measurement data on a continuous basis, said measurement data being recorded with a measurement range coordinated to the particle beam intensity.

This is carried out as follows: when a switch becomes necessary, the first measurement device is switched first from the first measurement range 43 to the second measurement range 45 (represented by the above bar 61). During this switching operation the second measurement device continues measuring in the original measurement range and its signal is used to control the beam. Quite generally the output signals of the beam monitoring device 32 are used to control the irradiation system, e.g. the acceleration device and/or the scanning device 30.

Subsequently, which means after the switch of measurement ranges of the first measurement device has taken place, the measurement range of the second measurement device is switched (represented by the lower bar 59). During this switching operation the first measurement device measures in the new measurement range and monitors the beam quality. When both measurement devices are operating in the new measurement range, both measurement devices are again available for a redundant measurement of the beam quality. In other words, the switching operations of the respective measurement ranges of the first and second measurement device take place at staggered intervals, as can be recognized by the displacement of branches to the two bars 59 and 61 in FIG. 5.

Switching back to the original measurement range or a switching to a further measurement range occurs analogously.

It is possible to continuously monitor the beam quality by the successive switching of measurement ranges. Only during the comparatively brief switching operation a redundant measurement is dispensed with.

Figure 6:
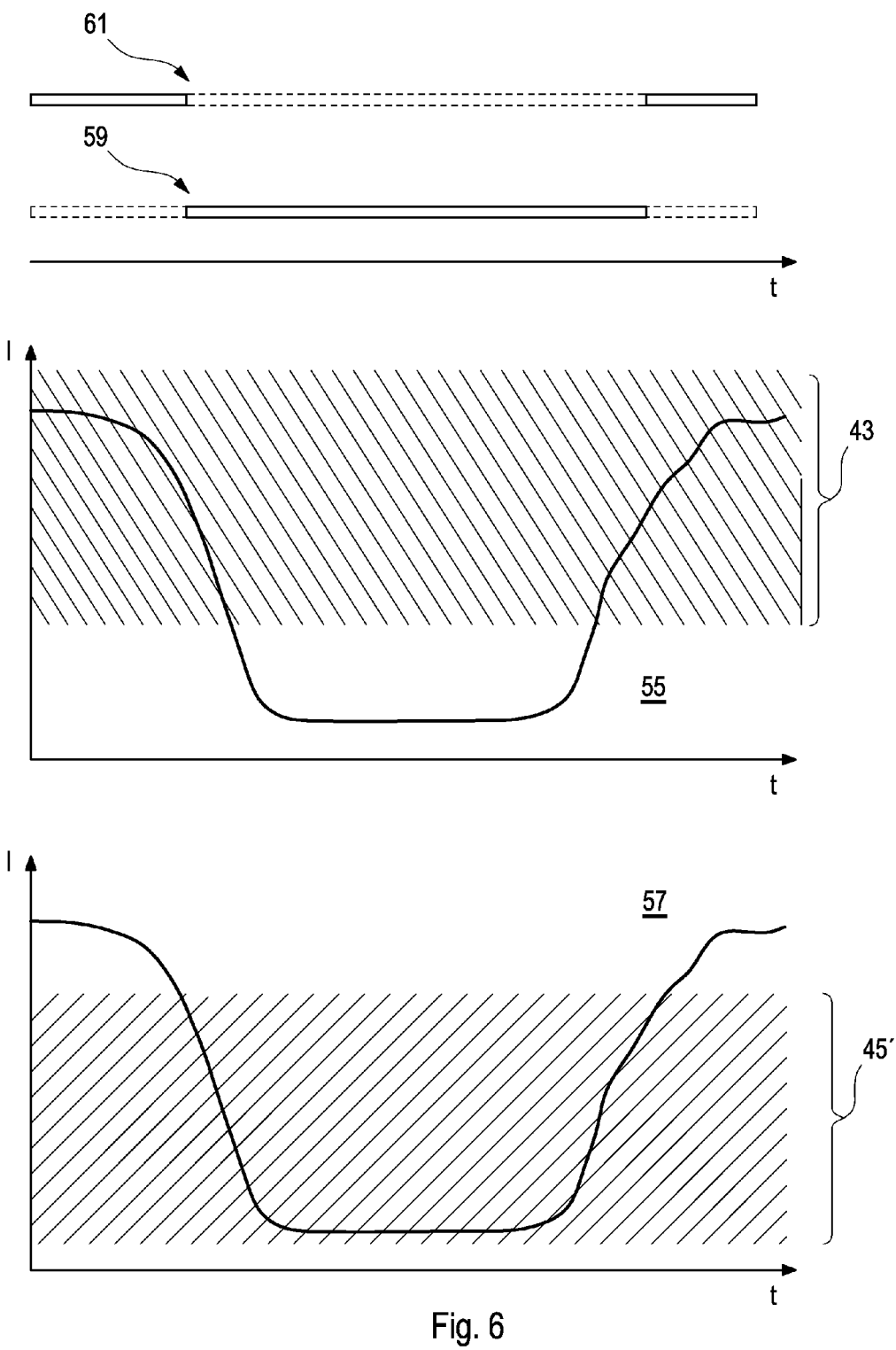
FIG. 6 shows a representation of a further embodiment in which two measurement devices are used.

FIG. 6 shows an embodiment in which the beam monitoring device likewise has two measurement devices, which however are operated here in two different measurement ranges 43, 45' for parallel monitoring of the beam quality.

In this embodiment, in the event of a change of the particle beam intensity from one measurement range 43 to the other measurement range 45', a measurement device is present which is already being operated in the other measurement range. As a result, where applicable a switching of measurement ranges of the individual measurement devices 34, 36 can be dispensed with.

The measurement device which is being operated with the adequate measurement range for the intensity of the particle beam is operated as the main measurement device, while the other measurement device, which is being operated in the measurement range that is not optimal for the particle beam intensity functions as a redundancy measurement device.

While it is true that with the redundancy measurement measuring device the required accuracy for monitoring the beam quality may not be achieved, the data recorded in the non-optimal measurement range can be sufficient for the redundancy measurement. For example with the redundancy measurement device the applied dose can still be checked within an order of magnitude, and hence in the case of relevant false dosing the beam can be switched off.

For the case that the beam intensity changes such that it exits the measurement range of the main measurement device and enters the measurement range of the redundancy measurement device, a change of measurement devices takes place. The redundancy measurement device is now operated as a main measurement device and vice versa. In this way a continuous measurement of the beam intensity can take place.

In the example shown here, in the event of high intensity the first measurement device, which is operated in the first measurement range 45 (middle part 55 of the representation), is operated as the main measurement device (upper bar 61, solid lines), while in the event of low intensity the first measurement device is operated as the redundancy measurement device (upper bar 61, dashed line). For the second measurement device, which is being operated in the second measurement range 45', it is conversely(lower part 57 of the representation, lower bar 59).

Figure 7:
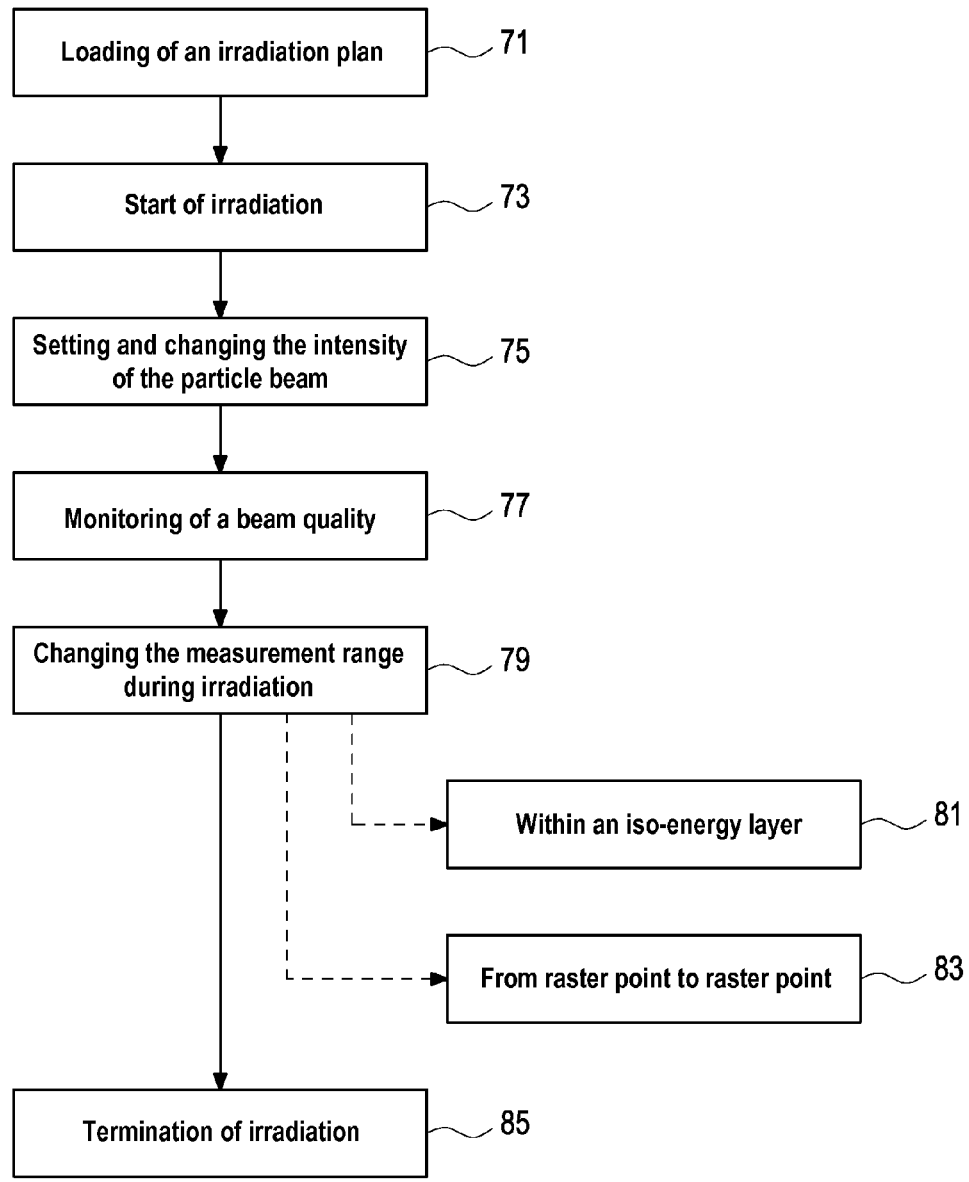
FIG. 7 shows a schematic representation of procedural steps which are employed in carrying out the method.

In FIG. 7 procedural steps which are carried out in the case of one embodiment of the method are illustrated with the help of a schematized representation.

In a first step an irradiation plan is loaded. The irradiation plan comprises a plurality of target points for which information is stored as to where the particle beam is supposed to be directed to, how many particles are supposed to be deposited at the respective target point and how often the target point should be approached (Step 71).

Based on this information in a second step the particle beam is generated and provided by the particle therapy system, so that the irradiation can be started (Step 73). The intensity of the extracted particle beam is set depending on the requirements which are stored for a specified target point (Step 75). During the irradiation of the target volume the intensity of the particle beam can thus change from target point to target point.

During the application of the particle beam a beam quality of the particle beam is monitored with a beam monitoring device (Step 77). As an example, this can be the position of the particle beam, which is monitored using a multiwire proportional chamber, or this can be the intensity of the particle beam, which is monitored with an ionization chamber. The measurement range of the beam monitoring device is set to the intensity of the particle beam (Step 79).

During the irradiation of the target volume the measurement range of the beam monitoring device and the intensity of the particle beam are adjusted during the course of the irradiation. It can happen that the measurement range of the beam monitoring device is changed during the irradiation of an iso-energy layer (Step 81) or at least sometimes from target point to target point, for example in the case of great differences in the particle count to be deposited from target point to target point (Step 83), or within a rescanning pass when an irradiation is carried out in the rescanning method.

After the dose to be deposited in the target volume has been deposited in accordance with the irradiation plan, the irradiation is terminated (Step 85).

It is obvious to a person skilled in the art that the foregoing described embodiments are to be taken as examples and that the present disclosure is not restricted to said embodiments, but rather can be varied in many and varied ways without leaving the protective scope of the claims. Further it is obvious that the features, whether disclosed in the description, in the claims, in the figures or elsewhere also define individually useful components of the present disclosure, even if they are described jointly together with other features.

We claim:

1. An irradiation system, comprising
    an accelerator device with a particle accelerator, with which particles can be accelerated and with which a particle beam can be generated, wherein the particle beam has a beam intensity,
    at least one beam monitoring device for the measurement of a beam quality of the particle beam, wherein the beam quality includes at least one of a beam intensity or a transverse beam position. wherein the beam monitoring device comprises at least two measurement devices for measurement of the same beam quality and exhibits several adjustable measurement ranges, and
    a control device for controlling the accelerator device and the beam monitoring device,
    wherein control is carried out during an irradiation of a target volume,
    wherein the measurement range of the beam monitoring device can be set depending on a particle count to be applied per target point in the target volume, and
    wherein the measurement range of the beam monitoring device can be altered during the irradiation of the target volume, and
    wherein the measurement ranges assigned to the measurement devices can be set at least temporarily such that the measurement devices are operated in different measurement ranges, so that different, simultaneously active measurement ranges are present within the beam monitoring device.

2. The irradiation system according to claim 1 wherein the control device is designed to carry out the irradiation of a target volume slice by slice in iso-energy layers and wherein the measurement range can be altered within an iso-energy layer.

3. The irradiation system according to claim 1 wherein the control device is designed to carry out irradiation in the rescanning method, in which a region of a target volume is irradiated in several consecutive rescan passes, wherein the measurement range can be altered within a rescan pass.

4. The irradiation system according to claim 1 wherein the control device is designed to alter the beam intensity during the irradiation and to switch the beam monitoring device from a first measurement range to a second measurement range during the irradiation, as soon as the beam intensity changes such that the beam intensity exits the first measurement range and/or enters the second measurement range.

5. The irradiation system according to claim 1 wherein the control device is designed to carry out a beam interruption in the event of switching the measurement range.

6. The irradiation system according to claim 1 wherein the control device is designed to switch the measurement range in the case of an activated particle beam.

7. The irradiation system according to claim 1, wherein one of the measurement devices can be operated as the main measurement device and another one of the measurement devices can be operated as a redundancy measurement device, and wherein a change of measurement range of the beam monitoring device takes place by means of a change of the measurement device being operated as the main measuring device.

8. The irradiation system according to claim 1 wherein in the event of a switching of the measurement range of the beam monitoring device a switch of the measurement ranges assigned to the measurement devices takes place at staggered intervals.

9. A control method for controlling an irradiation system, comprising the following steps:
    generation of a particle beam, wherein the particle beam comprises a beam intensity,
    monitoring of a beam quality of the particle beam with a beam monitoring device that includes at least two measurement devices for measurement of the same beam quality, wherein one of several adjustable measurement ranges is selected, wherein the beam quality includes at least one of a beam intensity or a transverse beam position,
    wherein control is carried out during an irradiation of a target volume,
    wherein the measurement range of the beam monitoring device can be altered during the irradiation of the target volume,
    wherein the measurement range of the beam monitoring device is set depending on a particle count to be applied per target point in the target volume, and
    wherein the measurement ranges assigned to the measurement devices are set at least temporarily such that the measurement devices are operated in different measurement ranges, so that different, simultaneously active measurement ranges are present within the beam monitoring device.

10. The control method according to claim 9, wherein irradiation is carried out in the raster scan method.

11. The control method according to claim 9 wherein the control method is carried out during irradiation of a target volume, wherein irradiation is carried out slice by slice in iso-energy layers and wherein the measurement range is altered within an iso-energy layer.

12. The control method according to claim 9, wherein in the event of a switching of the measurement range of the beam monitoring device a switch of the measurement ranges assigned to the measurement devices takes place at staggered intervals.

* * * * *